United States Patent
Kim et al.

(10) Patent No.: US 9,133,549 B2
(45) Date of Patent: Sep. 15, 2015

(54) GAS SENSOR USING METAL OXIDE NANOPARTICLES, AND METHOD FOR MANUFACTURING SAME

(75) Inventors: Il-Doo Kim, Seoul (KR); Dong-Young Kim, Seoul (KR); Sung-Yeon Jang, Daegu (KR); Seong-Mu Jo, Seoul (KR); Jae-Min Hong, Seoul (KR); Yun-Seok Lee, Gimpo-si (KR); Sung-Chul Yang, Seoul (KR)

(73) Assignees: AMOGREENTECH CO., LTD., Gyeonggi-do (KR); Korea Institute of Science and Technology, Seoul (KR)

( * ) Notice: Subject to any disclaimer, the term of this patent is extended or adjusted under 35 U.S.C. 154(b) by 0 days.

(21) Appl. No.: 13/266,815

(22) PCT Filed: Apr. 30, 2010

(86) PCT No.: PCT/KR2010/002766
§ 371 (c)(1),
(2), (4) Date: Oct. 28, 2011

(87) PCT Pub. No.: WO2010/126336
PCT Pub. Date: Nov. 4, 2010

(65) Prior Publication Data
US 2012/0042713 A1    Feb. 23, 2012

(30) Foreign Application Priority Data
Apr. 30, 2009 (KR) .......................... 10-2009-0038043

(51) Int. Cl.
| | |
|---|---|
| G01N 33/00 | (2006.01) |
| C23C 24/04 | (2006.01) |
| C23C 4/12 | (2006.01) |
| C23C 4/18 | (2006.01) |
| C23C 24/00 | (2006.01) |
| C23C 26/00 | (2006.01) |
| G01N 27/12 | (2006.01) |

(52) U.S. Cl.
CPC ............... *C23C 24/04* (2013.01); *C23C 4/121* (2013.01); *C23C 4/18* (2013.01); *C23C 24/00* (2013.01); *C23C 26/00* (2013.01); *G01N 27/127* (2013.01); *G01N 33/0036* (2013.01)

(58) Field of Classification Search
CPC ............ G01N 27/414; G01N 33/0009; G01N 33/0027
USPC ........................................................ 73/31.06
See application file for complete search history.

(56) References Cited

U.S. PATENT DOCUMENTS

2008/0171656 A1*  7/2008  Wang et al. ................... 502/326

FOREIGN PATENT DOCUMENTS

| KR | 10-2007-0066859 A | 6/2007 |
|---|---|---|
| KR | 10-2008-0052249 A | 6/2008 |

(Continued)

*Primary Examiner* — Laura Martin
*Assistant Examiner* — Alex Devito
(74) *Attorney, Agent, or Firm* — Dickstein Shapiro LLP

(57) ABSTRACT

The present invention provides a gas sensor, including: a sensor substrate provided with an electrode; and a thin layer of sensor material formed by spraying a solution in which metal oxide nanoparticles are dispersed onto the sensor substrate. The gas sensor is advantageous in that a sensor material is formed into a porous thin layer containing metal oxide nanoparticles having a large specific surface area, thus realizing high sensitivity on the ppb scale and a high reaction rate. Further, the gas sensor is advantageous in that it can be manufactured at room temperature, and the thickness of a sensor material can be easily adjusted by adjusting the spray time, so that a thin gas sensor or a thick gas sensor can be easily manufactured.

8 Claims, 5 Drawing Sheets

(56) References Cited

FOREIGN PATENT DOCUMENTS

| KR | 10-2009-0011631 A | 2/2009 |
| KR | 10-2010-0044944 A | 5/2010 |
| WO | WO 2007073111 A1 * | 6/2007 |

* cited by examiner

【FIG. 3】
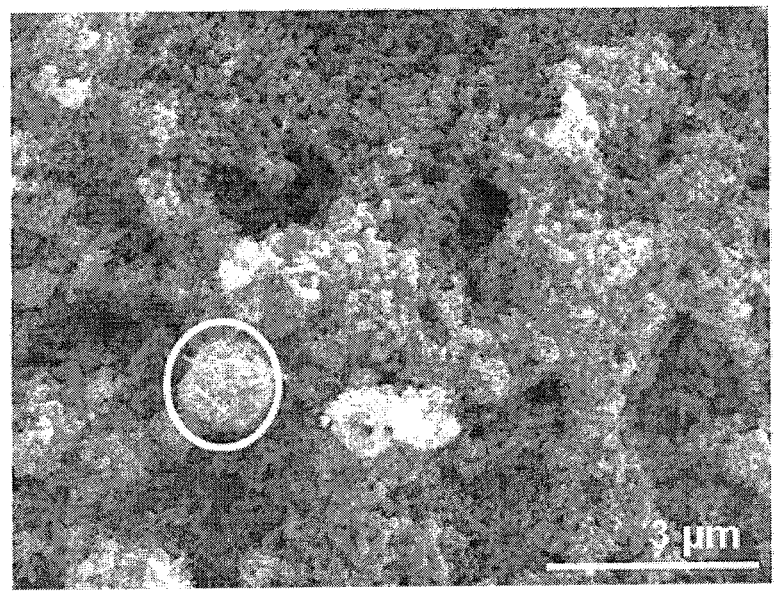
【FIG. 4】
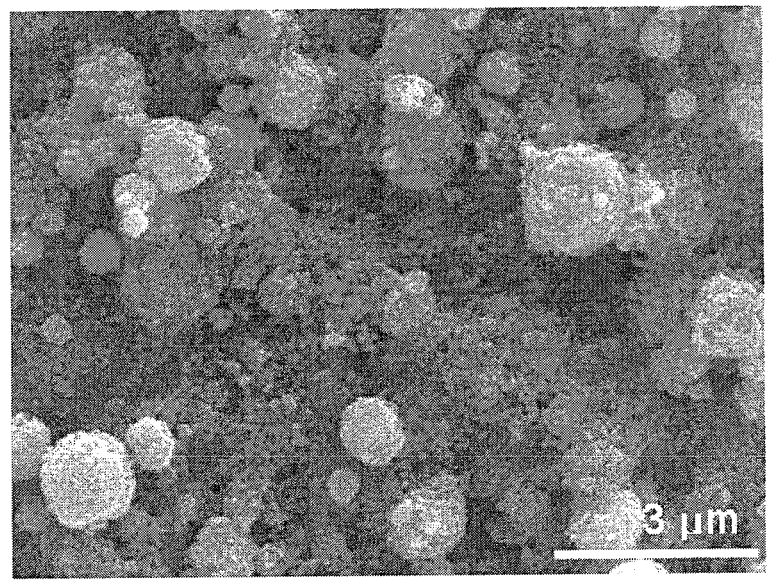

[FIG. 5]
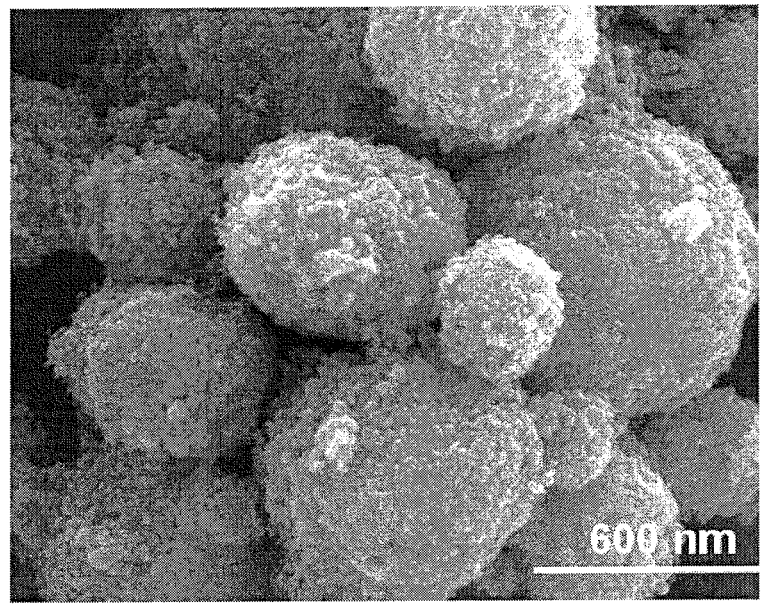
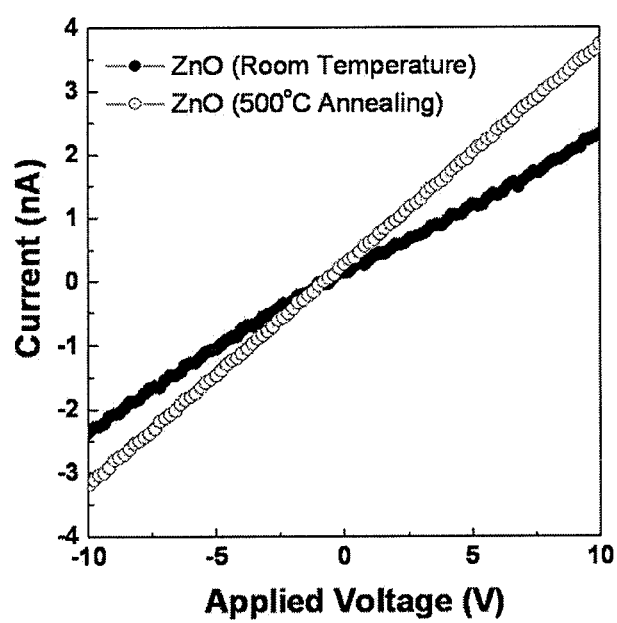
[FIG. 6]

【FIG. 7】
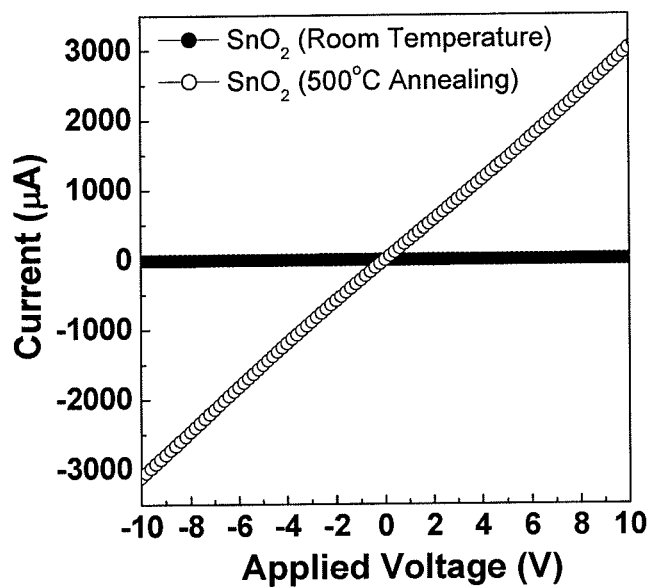
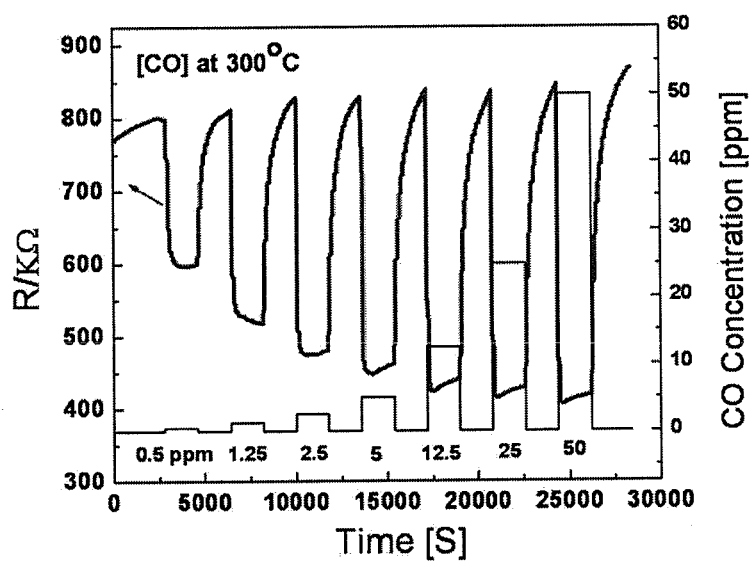
【FIG. 8】

[FIG. 9]
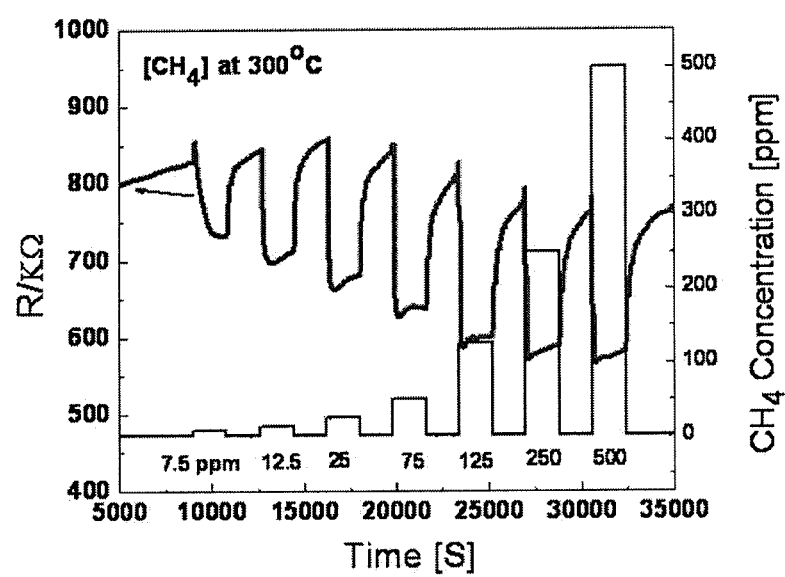

GAS SENSOR USING METAL OXIDE NANOPARTICLES, AND METHOD FOR MANUFACTURING SAME

TECHNICAL FIELD

The present invention relates to a gas sensor and a method of manufacturing the same. More particularly, the present invention relates to a gas sensor, which can ultrasensitively detect hydrogen ($H_2$), oxygen ($O_2$) and harmful environmental gases ($NO_x$, CO, $CO_2$, HC, $SO_x$, VOCs, etc.) using a metal oxide nanoparticle thin layer formed by spraying a solution containing metal oxide nanoparticles, and to a method of manufacturing the same.

BACKGROUND ART

The excess emission of carbon dioxide is accelerating global warming, and harmful exhaust gases and environment gases that were discharged from automobiles and industry are threatening human health. Under such circumstances, it is very important to detect the above harmful gases early and to respond appropriately to them. In particular, it is becoming important every day to measure the level of air pollution in real time and to warn when the air pollution exceeds an allowable level. In order to detect the above gases early, an ultrasensitive sensor that can rapidly and accurately monitor an extremely small amount of harmful gas at the level of sub-ppm is required.

Currently, commonly-used metal oxide semiconductor gas sensors measure the concentration of gases by detecting the change in resistance occurring when external gases are adsorbed onto the surface of metal oxides. Among metal oxides (ZnO, $SnO_2$, $WO_3$, $TiO_2$, etc.), materials having a band-gap of 3.0~4.8 eV have semiconductor properties. When external gases ($NO_x$, CO, $H_2$, HC, $SO_x$, etc.) are adsorbed on the surface of such a metal oxide having semiconductor properties, the resistance of the metal oxide is changed by an oxidation-reduction process. The sensitivity of a sensor increases as the change in resistance of the metal oxide increases. Therefore, in order to improve the sensitivity of a sensor, it is preferable to increase the specific surface area of a metal oxide and to allow a sensor to have a porous structure such that gas easily moves on the surface of a metal oxide.

Electrical sensors using nanowires or nanotubes are characterized in that they can be fabricated in the form of an ultrasensitive nanosensor because the specific surface area of nanowires or nanotubes is relatively large. However, forming such nanostructures is generally accompanied by complicated processes and heat treatment must be conducted at a high temperature of 600° C. or above.

In order to miniaturize a gas sensor, it is important to form a sensor material including a gas-sensitive material into a thin layer. Such a thin layer is generally formed by screen printing, spin coating, sputtering, pulsed laser deposition (PLD), chemical vapor deposition (CVD) or the like. Further, the thin layer may be formed by an electrospray process.

Screen printing is problematic in that it is difficult to form a sensor material layer to a thickness of less than 500 nm, and in that additional heat treatment is required in order to remove a binder and improve the adhesiveness between the sensor material layer and a substrate after screen printing.

Even when a sensor thin film is formed using spin coating, sputtering, pulsed laser deposition (PLD), chemical vapor deposition (CVD) or the like, there are problems in that high-temperature heat treatment is required in order to obtain a nanocrystalline structure, and in that high-temperature of 450° C. is required even in-situ deposition.

More concretely, U.S. Pat. No. 7,259,109 discloses a method of forming a thin film by preparing a precursor-containing solution and then directly spraying the solution onto a semiconductor substrate. However, this method is used to form a thin film having a low dielectric constant.

Korean Patent Registration No. 10-0843191 discloses a method of manufacturing a nanofiber fiter medium containing silver nanoparticles, comprising the steps of: forming a nanofiber layer by electrospinning; and electrospraying a silver nanoparticle-containing solution onto the nanofiber layer to diffuse silver nanoparticles into the surface of the nanofiber layer. However, in this method, only silver nanoparticles are used as the metal nanoparticles.

Korean Patent Registration No. 10-0583910 discloses a method for patterning nanosized structures by electrospraying nanoparticles in order to overcome the limit of the line width of a pattern, to maintain high reproducibility and solve the problem of noise pattern occurrence. In this method, gold nanoparticles having a size of 20 nm are used as metal nanoparticles.

However, since the metal particles, such as silver (Ag) particles, gold (Au) particles and the like, mentioned in the above Patent documents, react with environmental pollutants, such as alcohols, $NO_x$, $SO_x$, $NH_3$, $CO_2$, DMMP, phenol, acetone, formaldehyde, hydrogen gas and the like, it is difficult for them to change the resistance. Therefore, they cannot be used as sensor materials.

Meanwhile, a thin film, formed by electrospraying a solution in which metal ions as metal oxide precursors are dissolved, has a surface structure which is not greatly different from that of a sensor thin layer obtained by a general sol-gel reaction or a sensor thin layer formed by sputtering or chemical vapor deposition (CVD), and has high density. Therefore, there is a problem in that it is difficult to manufacture an ultrasensitive sensor which can measure harmful gases at the ppm sensitivity level.

DISCLOSURE

Technical Problem

Accordingly, the present invention has been developed to solve the above-mentioned problems, and a first object of the present invention is to provide a high-sensitive gas sensor, which includes a sensor material that has a porous structure and contains metal oxide nanoparticles having a large specific surface area, and which can detect harmful gases at the ppb level.

A second object of the present invention is to provide an ultrasensitive gas sensor, which has high mechanical and electrical stability because the adhesivity between a sensor substrate provided with an electrode and a sensor material containing metal oxide nanoparticles is greatly increased.

A third object of the present invention is to provide a method of manufacturing a gas sensor, which can manufacture the above-mentioned high-sensitive gas sensor at room temperature, which can easily adjust the thickness of a sensor material to form a thin film or a thick film, and, if necessary, which can adjust the characteristics of a sensor material by conducting heat treatment.

A fourth object of the present invention is to provide a method of manufacturing a gas sensor, which can produce the above-mentioned high-sensitive gas sensor in a high yield and at low cost using a simple process.

Technical Solution

In order to accomplish the above objects, an aspect of the present invention provides a gas sensor, including: a sensor substrate provided with an electrode; and a thin layer of sensor material formed by spraying a solution in which metal oxide nanoparticles are dispersed onto the sensor substrate.

Another aspect of the present invention provides a method of manufacturing a gas sensor, including the steps of: preparing a solution in which metal oxide nanoparticles are uniformly dispersed in a solvent; and spraying the solution onto a sensor substrate provided with an electrode to form a thin layer of sensor material.

The method may further include the step of heat-treating the sensor material at a temperature of 80° C.~300° C.

The method may further include the step of heat-treating the sensor material at a temperature of 350° C.~600° C.

The method may further include the step of adhering the sensor material closely to the sensor substrate by thermal pressing.

Advantageous Effects

According to the gas sensor of the present invention, since a sensor material is formed in a porous thin layer containing metal oxide nanoparticles having a large specific surface area, the gas sensor can realize the high sensitivity of ppb and a high reaction rate.

Further, according to the gas sensor of the present invention, since the gas sensor can be applied to various kinds of gases by changing the kinds of metal oxide nanoparticles used as the material of the sensor, it is possible to impart the gas sensor with the ability to be selective to specific gases.

Further, according to the gas sensor of the present invention, since the gas sensor is manufactured by directly spraying metal oxide nanoparticles onto a sensor electrode by electrostatic spray deposition, the adhesivity between a sensor substrate and a thin layer composed of metal oxide nanoparticles is greatly improved, and thus the electrical and mechanical stability of the gas sensor becomes high.

According to the method of manufacturing a gas sensor of the present invention, a gas sensor can be manufactured easily and cheaply because the gas sensor is manufactured by electrostatic spray deposition at room temperature. Further, in this method, it is possible to easily form a metal oxide thin layer having a thickness of 10 nm~several μm by adjusting the spray time.

Further, according to the method of manufacturing a gas sensor of the present invention, it is possible to further improve the electrical, thermal and mechanical stability of a gas sensor by the addition of thermal pressing, first heat treatment and/or second heat treatment.

DESCRIPTION OF DRAWINGS

FIG. 3 is a scanning electron microscope (SEM) photograph of a zinc oxide (ZnO) nanoparticle thin layer, which is a sensor material prepared by electrospraying a solution containing zinc oxide (ZnO) nanoparticles according to Example 1 of the present invention;

FIG. 4 is a scanning electron microscope (SEM) photograph of a tin oxide ($SnO_2$) nanoparticle thin layer, which is a sensor material prepared by electrospraying a solution in which tin oxide ($SnO_2$) nanoparticles are dispersed according to Example 2 of the present invention;

FIG. 5 is a scanning electron microscope (SEM) photograph of the tin oxide ($SnO_2$) nanoparticle thin layer prepared in Example 2, which has been heat-treated at 500° C.;

FIG. 6 is a graph showing the results of current-voltage characteristics (Test Example 1) of the zinc oxide nanoparticle thin layers prepared in Example 1 and those of the zinc oxide nanoparticle thin layers prepared in Example 2 which have been heat-treated at 500° C. by an additional process;

FIG. 7 is a graph showing the results of current-voltage characteristics (Test Example 2) of the tin oxide nanoparticle thin layers prepared in Example 3 and those of the tin oxide nanoparticle thin layers prepared in Example 4 which have been heat-treated at 500° C. by an additional process;

FIG. 8 is a graph showing the results of measuring changes in resistance while changing the CO concentration from 0.5 ppm to 50 ppm at 300° C., using a gas sensor manufactured using the tin oxide ($SnO_2$) nanoparticle thin layer (Test Example 3); and FIG. 9 is a graph showing the results of measuring changes in resistance while changing the $CH_4$ concentration from 7.5 ppm to 500 ppm at 300° C., using a gas sensor manufactured using the tin oxide ($SnO_2$) nanoparticle thin layer (Test Example 4).

BEST MODE

Figure 1:
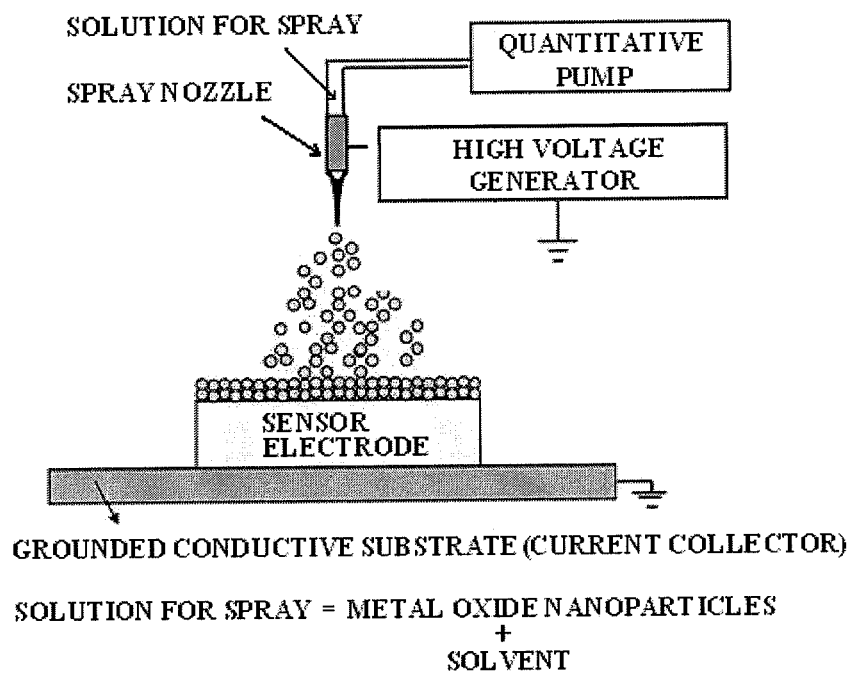
FIG. 1 is a schematic view showing a process of manufacturing a gas sensor by electrospraying solution in which metal oxide nanoparticles are dispersed onto a sensor substrate according to the present invention.

Hereinafter, the present invention will be described in detail.

I. Gas Sensor

The gas sensor of the present invention includes a sensor substrate provided with an electrode which can measure changes of in resistance, and a thin layer of sensor material formed by spraying a solution in which metal oxide nanoparticles are dispersed onto the sensor substrate. The electrode may be made of one or more selected from the group consisting of platinum (Pt), gold (Au), palladium (Pd), iridium (Ir), silver (Ag), ruthenium (Ru), nickel (Ni), stainless steel (STS), aluminum (Al), molybdenum (Mo), chromium (Cr), copper (Cu), titanium (Ti), tungsten (W), ITO (Sn-doped $In_2O_3$) and FTO (F-doped $SnO_2$), and the sensor substrate may be a ceramic substrate, an alumina ($Al_2O_3$) substrate, a silicon (Si) substrate deposited with an insulation layer, or a silicon oxide ($SiO_2$) substrate. Preferably, a substrate provided with an interdigital electrode may be used as the sensor substrate.

In the gas sensor of the present invention, two or more of the sensor substrates may be arrayed, and each of them may be provided thereon with a thin layer of sensor material which is made of different metal oxide nanoparticles from that used in a thin layer of sensor material of the other sensor substrates.

The gas sensor of the present invention can exhibit high mechanical stability because fine metal oxide nanoparticles are uniformly deposited on the sensor substrate by an electrostatic force. Further, since the gas sensor can be manufactured at room temperature, the production cost thereof can be greatly reduced, and the production yield thereof can be greatly increased. It is preferred that metal oxide nanoparticles having an average diameter of 1~200 nm, more preferably less than 100 nm, be used as the metal oxide nanoparticles. When the average diameter of the metal oxide nanoparticles is within the above range, the gas sensor manufactured using these metal oxide nanoparticles can exhibit high sensitivity, and can increase selectivity by means of an array structure.

II. Method of Manufacturing a Gas Sensor

The method of manufacturing a gas sensor according to the present invention includes the steps of: preparing a solution in which metal oxide nanoparticles are uniformly dispersed in a solvent; and spraying the solution onto a sensor substrate provided with an electrode to form a sensor material.

If necessary, the method may further include the steps of: adhering the sensor material closely to the sensor substrate by thermal pressing; heat-treating the sensor material at a temperature of 80° C.~300° C.; and/or heat-treating the sensor material at a temperature of 350° C.~600° C.

Hereinafter, each step of the method of manufacturing a gas sensor according to the present invention will be described in detail.

1) Preparing a Solution in which Metal Oxide Nanoparticles are Dispersed

A solution including metal oxide nanoparticles and a solvent is prepared.

As the metal oxide nanoparticles, any kind of metal oxide nanoparticles can be used as long as they have the characteristics of a semiconductor. Specific examples of the metal oxide nanoparticles may include $SnO_2$, $TiO_2$, ZnO, $VO_2$, $In_2O_3$, NiO, $MoO_3$, $SrTiO_3$, Fe-doped $SrTiO_3$ $SrTiO_3$ ($SrTi_{0.65}Fe_{0.35}O_3$), $Fe_2O_3$, $WO_3$ and CuO nanoparticles. They may be used independently or in a combination of two or more. The metal oxide nanoparticles may be formed in the shape of grain or rod. The size of the metal oxide nanoparticles may be 1~200 nm, and is not particularly limited as long as they can be uniformly dispersed in a solvent.

Examples of the solvent may include, but are not limited to, ethanol, methanol, propanol, butanol, isopropyl alcohol (IPA), dimethylformamide (DMF), acetone, tetrahydrofuran, toluene, and water. They may be used independently or in a combination of two or more.

In the solution, the mixing ratio of the metal oxide nanoparticles and the solvent is not particularly limited as long as the metal oxide nanoparticles can be uniformly dispersed in the solvent. Generally, the metal oxide nanoparticles may be included in an amount of 0.1~10 wt % based on the total amount of the solution.

In order to easily electrospray the solution, it is important to uniformly disperse the metal oxide nanoparticle in the solvent. For this purpose, conglomerated metal oxide nanoparticle may be dispersed by ultrasonication. Further, when the metal oxide nanoparticles having a size of 30 nm~several μm are distributed, the size of the metal oxide nanoparticles may be decreased by ball milling or microbead milling.

The solution may further include a dispersant such that the metal oxide nanoparticles are uniformly dispersed in the solvent. As the dispersant, dispersants commonly known in the related field may be used without limitation. Specific examples of the dispersant may include Triton X-100, acetic acid, cetyltrimethyl ammonium bromide (CTAB), isopropyltris(N-aminoethyl-aminoethyl) titanate (INAAT, Ajimoto fine-techno Co., Inc.), 3-aminopropyltriethoxy-silane (APTS, Aldrich, 99%), polyvinyl pyrrolidone (PVP), and poly(4-vinylphenol). They are may be used independently or in a combination of two or more.

2) Forming a Metal Oxide Nanoparticle Thin Layer Using Spraying

In the method of manufacturing a gas sensor according to the present invention, the spraying of the solution may be conducted by electrospraying, air-flash spraying or the like, preferably electrospraying.

FIG. 1 is a schematic view showing an electrospraying apparatus used to obtain a metal oxide nanoparticle thin layer in the method of manufacturing a gas sensor according to the present invention.

The prepared solution is sprayed onto a substrate provided with a sensor electrode.

As shown in FIG. 1, the electrospraying apparatus includes a spray nozzle connected to a quantitative pump for quantitatively introducing the solution, a high voltage generator, a grounded conductive substrate, and the like. First, a sensor electrode is disposed on the grounded conductive substrate. In this case, the grounded conductive substrate is used as a negative electrode, and the spray nozzle provided with a pump that can adjust the amount of the solution discharged per hour is used as a positive electrode. A voltage of 8~30 kV is applied, the feed rate of the solution is adjusted to 10~100 μl/min, and then the solution is sprayed onto the conductive substrate provided with the sensor electrode until the thickness of a metal oxide nanoparticle thin layer is 0.1~10 μm.

3) Heat Treatment

The method of manufacturing a gas sensor according to the present invention, if necessary, may further include the steps of: primarily heat-treating the metal oxide nanoparticle thin layer (sensor material) at a temperature of 80° C.~300° C.; and/or secondarily heat-treating the metal oxide nanoparticle thin layer (sensor material) at a temperature of 350° C.~600° C.

This heat treatment includes: a high-temperature drying process (primary heat treatment) that is carried out at a temperature of 80° C.~300° C. in order to completely remove the solvent remaining on the substrate after spraying the solution; and a heat treatment process (secondary heat treatment) that is carried out at a temperature of 350° C.~600° C. in order to increase the bonding force between metal oxide nanoparticles, to increase the adhesion between the metal oxide nanoparticle thin layer and the substrate and to improve the electrical characteristics of the metal oxide nanoparticle thin layer by the growth of the metal oxide nanoparticles.

However, the primary heat treatment and/or the secondary heat treatment may be omitted when the metal oxide nanoparticle thin layer formed by spraying the solution has mechanical, electrical and thermal characteristics that are sufficiently stable.

4) Thermal Pressing

The method of manufacturing a gas sensor according to the present invention, if necessary, may further include the step of: attaching the metal oxide nanoparticle thin layer (sensor material) to the substrate by thermal pressing. The pressure, temperature and time for which the thermal pressing is conducted may be appropriately selected in consideration of the characteristics of the used metal oxide nanoparticles. For example, the thermal pressing may be conducted under the conditions of a temperature of 20° C.~150° C., a pressure of 0.01 MPa~10 Mpa and a pressing time of 10 seconds~10 minutes.

Such thermal pressing serves to improve the adhesion between the metal oxide nanoparticle thin layer (sensor material) and the substrate and to improve the electrical and mechanical characteristics of the metal oxide nanoparticle thin layer.

Further, the thermal pressing may also be simultaneously conducted together with the above-mentioned heat treatment processes, that is, primary heat treatment that is carried out at a temperature of 80° C.~300° C. in order to completely remove the solvent remaining on the substrate after spraying the solution and/or secondary heat treatment that is carried out at a temperature of 350° C.~600° C. in order to increase the bonding force between metal oxide nanoparticles, to increase the adhesion between the metal oxide nanoparticle thin layer and the substrate and to improve the electrical characteristics of the metal oxide nanoparticle thin layer by growing the metal oxide nanoparticles.

MODE FOR INVENTION

Hereinafter, the present invention will be described in more detail with reference to the following Examples. However, these Examples are set forth to illustrate the present invention, and the scope of the present invention is not limited to these Examples. The scope of the present invention is defined by technical ideas of the following claims.

Example 1

Forming Zinc Oxide Nanoparticle Thin Layer 0.4 g of zinc oxide (ZnO) nanoparticles (Aldrich, <100 nm) was mixed with 10 mL of ethanol to prepare a solution for spray. In order to uniformly disperse the zinc oxide (ZnO) nanoparticles in ethanol, ultrasonication was carried out for 30 minutes. Since the size of commercially-available zinc oxide nanoparticles is less than 100 nm, the solution for spray was prepared without performing a pulverizing process.

The prepared solution was charged into a syringe, the syringe charged with the solution was mounted on an electrospraying apparatus, and then voltage was applied between a tip provided at the end of the syringe and a lower substrate to obtain a zinc oxide nanoparticle thin layer. In this case, the voltage was 12 Kv, the flow rate of the solution was 30 μl/min, and the distance between the tip and the lower substrate was 10 cm. An alumina ($Al_2O_3$) substrate provided with an interdigital electrode (width of finger: 200 μm, interval between fingers: 200 μm, length of finger: 8 mm, finger pairs: 7) made of Au(200 nm)/Ti(50 nm) was used as a sensor substrate.

Figure 2:
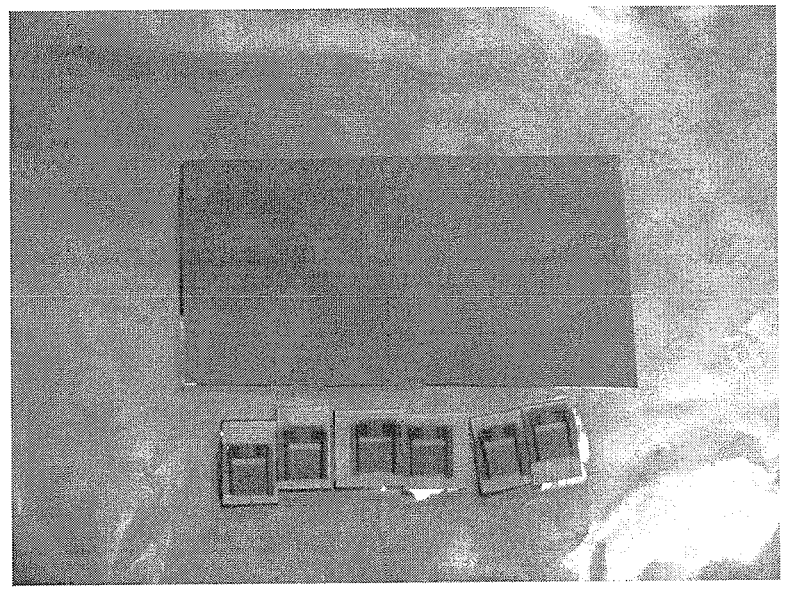
FIG. 2 is an optical microscope photograph of a zinc oxide (ZnO) nanoparticle thin layer formed on a sensor substrate and a current collector.

FIG. 2 is an optical microscope photograph of a substrate provided with a sensor electrode and a zinc oxide (ZnO) nanoparticle thin layer formed on a current collector (stainless steel) substrate. From FIG. 2, it can be ascertained that electrically charged metal oxide nanoparticles are accelerated by electrostatic force to be deposited on the substrate provided with the sensor electrode or the current collector, thus forming a uniform thin layer. In the case of a sensor material (metal oxide nanoparticle thin layer) deposited on an insulation substrate provided with an interdigital electrode, the characteristics of a sensor are evaluated by detecting the change in resistance of the metal oxide nanoparticle thin layer formed on an insulator between electrode layers.

FIG. 3 is a scanning electron microscope (SEM) photograph of the zinc oxide (ZnO) nanoparticle thin layer that was formed in Example 1. Referring to FIG. 3, it can be ascertained that the zinc oxide nanoparticle thin layer is divided into two parts, that is, one part in which nanoparticles conglomerate with each other in a size of 200~800 nm and the other part in which nanoparticles are formed into a thin layer without conglomerating with each other. Further, it can be ascertained that, regardless of the conglomeration of nanoparticles, nanoparticles are distributed in a size of 20~100 nm, and all of the nanoparticle thin layers are composed of ultrafine nanoparticles. Therefore, it can be seen that, since the sensor material of the present invention has porosity due to the metal oxide nanoparticles having high specific surface area and the fine pores between the metal oxide nanoparticles, it can be applied to various gas sensors.

Example 2

Heat Treatment (Secondary Heat Treatment) of Zinc Oxide Nanoparticle Thin Layer

The zinc oxide nanoparticle thin layer formed on the sensor substrate in Example 1 was heat-treated (secondarily heat-treated) at a temperature of 500° C. The heat treatment of the zinc oxide nanoparticle thin layer was carried out under an air atmosphere for 30 minutes using a box furnace.

Example 3

Forming Tin Oxide Nanoparticle Thin Layer 0.4 g of tin oxide ($SnO_2$) nanoparticles (Aldrich, <100 nm) was mixed with 10 mL of ethanol to prepare a solution for spray. In order to uniformly disperse the tin oxide ($SnO_2$) nanoparticles in ethanol, ultrasonication was carried out for 30 minutes.

The prepared solution for spray was charged into a syringe, the syringe charged with the solution was mounted on an electrospraying apparatus, and then voltage was applied between a tip provided at the end of the syringe and a lower substrate to obtain a tin oxide nanoparticle thin layer. In this case, the voltage was 12 Kv, the flow rate of the solution was 30 μl/min, and the distance between the tip and the lower substrate was 10 cm. An alumina ($Al_2O_3$) substrate provided with an interdigital electrode (width of finger: 200 μm, interval between fingers: 200 μm, length of finger: 8 mm, finger pairs: 7) made of Au(200 nm)/Ti(50 nm) was used as a sensor substrate. FIG. 4 shows a scanning electron microscope photograph of the obtained tin oxide nanoparticle thin layer.

Referring to FIG. 4, it can be ascertained that the tin oxide nanoparticle thin layer is divided into two parts, that is, one part in which nanoparticles conglomerate with each other in a size of 300~1.5 μm and the other part in which nanoparticles are formed into a thin layer without conglomerating with each other. Further, it can be ascertained that, regardless of the conglomeration of nanoparticles during the spray process, all of the nanoparticle thin layers are composed of ultrafine tin oxide nanoparticles having a size of 20~100 nm.

Example 4

Heat Treatment (Secondary Heat Treatment) of Tin Oxide Nanoparticle Thin Layer

The tin oxide nanoparticle thin layer formed on the sensor substrate in Example 3 was heat-treated (secondarily heat-treated) at a temperature of 500° C. The heat treatment of the tin oxide nanoparticle thin layer was carried out under an air atmosphere for 30 minutes using a box furnace.

FIG. 5 shows a scanning electron microscope (SEM) photograph of the tin oxide ($SnO_2$) nanoparticle thin layer prepared in Example 2, which has been heat-treated at 500° C. As shown in FIG. 5, after the heat treatment, the crystal growth of tin oxide nanoparticles occurs, and fine nanoparticles grow, so that the tin oxide nanoparticles are distributed in a size of 300 nm~2 μm. In the case of such a sensor material, it is expected that the electroconductivity of the sensor material is improved because nanoparticles are more easily bonded with each other. In particular, the sensor material maintains a high specific surface area because the grown particles are also composed of fine nanoparticles.

This heat treatment can improve the adhesive characteristics between the thin layer obtained by spraying at room temperature and the substrate provided with the sensor electrode.

In this Example, the heat treatment was carried out at a temperature of 500° C., but is not limited to any specific temperature. In order to completely remove the solvent remaining on the sensor substrate, the primary heat treatment in which the solution is dried at a temperature of 80° C.~300° C. may be included in the second heat treatment.

In the gas sensor using a metal oxide nanoparticle thin layer according to the present invention, in addition to the zinc oxide (ZnO) nanoparticles and tin oxide ($SnO_2$) nanoparticles, all kinds of metal oxide nanoparticles may be used as long as they are metal oxide nanoparticles having semiconductor characteristics. Specific examples of metal oxide nanoparticles may include $SnO_2$, $TiO_2$, ZnO, $VO_2$, $In_2O_3$, NiO, $MoO_3$, $SrTiO_3$, Fe-doped $SrTiO_3$, $Fe_2O_3$, $WO_3$ and CuO nanoparticles. When Fe-doped $SrTiO_3$ is used to manufacture an oxygen sensor, it may have a composition of $SrTi_{0.65}Fe_{0.35}O_3$.

The metal oxide nanoparticle thin layer formed by electrospraying can be used to manufacture a high sensitive sensor for detecting various environmental gases such as HC, $H_2$, $O_2$, CO, NOx, alcohol, $NH_3$, $CH_4$, $SO_x$, DMMP, phenol, acetone, formaldehyde, VOCs (volatile organic compounds). In particular, the environmental gases are not limited to specific gases as long as they are harmful environmental materials which can be detected by a change in resistance.

The electrical characteristics of each metal oxide thin layer were tested as follows.

Test Example 1

Evaluation of I-V Characteristics of Zinc Oxide Nanoparticle Thin Layer

In order to evaluate the electrical characteristics of the zinc oxide (ZnO) nanoparticle thin layer (sensor material) obtained in Example 1, the current-voltage (I-V) characteristics thereof were evaluated using Agilent B1500. The current change was measured while changing the applied voltage from −10V to +10V. Additionally, the current-voltage (I-V) characteristics of the heat-treated zinc oxide (ZnO) nanoparticle thin layer (sensor material) obtained in Example 2 were also evaluated.

FIG. 6 is a graph showing the current-voltage characteristics of the zinc oxide nanoparticle thin layer prepared in Example 1 and those of the zinc oxide nanoparticle thin layer (Example 2) which have additionally been heat-treated at 500☐. As shown in FIG. 6, the current values of the thin layers are 2.5 μA and 4 μA (heat-treated ZnO thin layer) at an applied voltage of 10V, so that these thin layers exhibit typical semiconductor characteristics. When hydrogen ($H_2$), oxygen ($O_2$) or harmful environmental gases ($NO_x$, CO, $CO_2$, HC, $SO_x$, VOCs, etc) are adsorbed onto the surface of each of the zinc oxide nanoparticle thin layers exhibiting semiconductor characteristics, a change in resistance occurs, so that the characteristics of a gas sensor can be evaluated. From FIG. 6, it can be ascertained that the electroconductivity of the zinc oxide nanoparticle thin layer heat-treated at 500☐ is somewhat improved compared to that of the zinc oxide nanoparticle thin layer formed at room temperature.

Test Example 2

Evaluation of I-V Characteristics of Tin Oxide Nanoparticle Thin Layer

In order to evaluate the electrical characteristics of the zinc oxide (ZnO) nanoparticle thin layers (sensor materials) obtained in Examples 3 and 4, the current-voltage (I-V) characteristics thereof were evaluated using Agilent B1500. The current change was measured while changing the applied voltage from −10V to +10V.

FIG. 7 is a graph showing the current-voltage characteristics of the zinc oxide nanoparticle thin layers prepared in Examples 3 and 4. As shown in FIG. 7, the current value of the tin oxide thin layer which has not been heat-treated is 2.5 nA at an applied voltage of 10V, so that this thin layer exhibited typical semiconductor characteristics. Further, the current value of the tin oxide thin layer which was heat-treated (500° C.) is 3000 μA at an applied voltage of 10V. Therefore, it can be ascertained that the electroconductivity of the tin oxide nanoparticle thin layer which has been heat-treated at 500° C. is greatly improved compared to that of the tin oxide nanoparticle thin layer which has not been heat-treated. The reason for this is because the contact characteristics between particles are improved by heat treatment.

Therefore, when hydrogen ($H_2$), oxygen ($O_2$) or harmful environmental gases ($NO_x$, CO, $CO_2$, HC, $SO_x$, VOCs, etc) are adsorbed on the surface of the tin oxide nanoparticle thin layers exhibiting semiconductor characteristics, changes in resistance occur, thus evaluating the characteristics of a gas sensor.

Test Example 3

CO Gas Sensor Using a Tin Oxide ($SnO_2$) Nanoparticle Thin Layer

A gas sensor was manufactured using each of the tin oxide ($SnO_2$) nanoparticle thin layers prepared in Examples 3 and 4, and then the change in resistance before and after reaction at 300° C. was measured using the gas sensor while changing carbon monoxide (CO) concentration. The gas sensor including the tin oxide nanoparticle thin layer was mounted in a quartz tube of a tube furnace. A Pt/Pt—Rh (type S) thermocouple measured temperature change while the gas sensor measured the change in resistance that occurred with various changes in a kind of gas and concentration of gas. Gas flow was controlled by MFC (Tylan UFC-1500A mass flow controller and Tylan RO-28 mass flow controller). The reaction was a reversible reaction, and the reaction time was very short. This measurement can also be carried out in a chamber provided with a heating element in addition to the tube furnace.

FIG. 8 is a graph showing the results of measuring the change in resistance while changing the CO gas concentration from 0.5 ppm to 50 ppm at 300° C., using the gas sensor manufactured using the tin oxide ($SnO_2$) nanoparticle thin layer. Referring to FIG. 8, the gas sensor using the tin oxide ($SnO_2$) nanoparticle thin layer shows typical N-type semiconductor characteristics that the resistance decreases when the gas sensor is exposed to a reducing gas (CO). In particular, it can be ascertained that the gas sensor can also easily measure a very small amount of CO (0.5 ppm) because it includes a tin oxide nanoparticle thin layer made of fine tine oxide nanoparticles.

Test Example 4

CH$_4$ Gas Sensor Using Tin Oxide (SnO$_2$) Nanoparticle Thin Layer

The change in resistance before and after reaction at 300° C. was measured using the same sensor and method as those of Test example 3, except that the change in resistance thereof was measured while changing the CH$_4$ gas concentration from 7.5 ppm to 500 ppm at 300° C.

FIG. 9 is a graph showing the results of measuring the change in resistance while changing the CH$_4$ gas concentration from 7.5 ppm to 500 ppm at 300° C., using the gas sensor manufactured using the tin oxide (SnO$_2$) nanoparticle thin layer. Referring to FIG. 9, the gas sensor using the tin oxide (SnO$_2$) nanoparticle thin layer shows typical N-type semiconductor characteristics that the resistance decreases when the gas sensor is exposed to methane gas (CH$_4$). In particular, it can be ascertained that the gas sensor can also easily measure a very small amount of CH$_4$ (7.5 ppm) because it includes a tin oxide nanoparticle thin layer made of fine tine oxide nanoparticles.

As ascertained in the above Examples and Test Examples, there are various kinds of metal oxide nanoparticles that can be used to obtain a thin layer (sensor material) for a gas sensor, and these are limited to specific metal oxide nanoparticles.

Although the preferred embodiment of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method of manufacturing a gas sensor, comprising the steps of:
   preparing a solution consisting of metal oxide nanoparticles and a solvent, in which the metal oxide nanoparticles are uniformly dispersed in the solvent; and
   spraying the solution onto a sensor substrate provided with an electrode by electrostatic spraying to form a thin layer of sensor material.

2. The method of manufacturing a gas sensor according to claim 1, further comprising the step of thermally pressing the sensor material.

3. The method of manufacturing a gas sensor according to claim 2, wherein the thermal pressing of the sensor material is conducted at a temperature of 20° C.~150° C. and a pressure of 0.01 MPa~10 MPa for 10 seconds~10 minutes.

4. The method of manufacturing a gas sensor according to claim 1, further comprising the step of heat-treating the sensor material at a temperature of 80° C.~300° C.

5. The method of manufacturing a gas sensor according to claim 1, further comprising the step of heat-treating the sensor material at a temperature of 350° C.~600° C.

6. The method of manufacturing a gas sensor according to claim 1, wherein the metal oxide nanoparticles are one or more selected from the group consisting of SnO$_2$, TiO$_2$, ZnO, VO$_2$, In$_2$O$_3$, NiO, MoO$_3$, SrTiO$_3$, Fe-doped SrTiO$_3$, Fe$_2$O$_3$, WO$_3$ and CuO nanoparticles.

7. The method of manufacturing a gas sensor according to claim 1, wherein the spraying of the solution is conducted by electrospraying or air-flash spraying.

8. The method of manufacturing a gas sensor according to claim 1, wherein the method is performed without a heat-treating step.

* * * * *